United States Patent
Zuo et al.

(10) Patent No.: US 11,008,272 B1
(45) Date of Patent: May 18, 2021

(54) VISIBLE-LIGHT-INDUCED DIRECT OXIDATION METHOD FOR SATURATED HYDROCARBON BONDS

(71) Applicant: SHANGHAITECH UNIVERSITY, Shanghai (CN)

(72) Inventors: Zhiwei Zuo, Shanghai (CN); Anhua Hu, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 169 days.

(21) Appl. No.: 16/478,476

(22) PCT Filed: Oct. 26, 2017

(86) PCT No.: PCT/CN2017/107760
§ 371 (c)(1),
(2) Date: Jul. 17, 2019

(87) PCT Pub. No.: WO2018/133473
PCT Pub. Date: Jul. 26, 2018

(30) Foreign Application Priority Data

Jan. 19, 2017 (CN) .......................... 201710045228.6

(51) Int. Cl.
| | |
|---|---|
| *C07C 45/33* | (2006.01) |
| *C07C 29/50* | (2006.01) |
| *C07C 67/313* | (2006.01) |
| *C07C 281/02* | (2006.01) |
| *C07C 67/307* | (2006.01) |
| *C07C 17/14* | (2006.01) |

(52) U.S. Cl.
CPC .............. *C07C 45/33* (2013.01); *C07C 17/14* (2013.01); *C07C 29/50* (2013.01); *C07C 67/307* (2013.01); *C07C 67/313* (2013.01); *C07C 281/02* (2013.01)

(58) Field of Classification Search
CPC ....... C07C 45/33; C07C 67/313; C07C 29/50; C07C 281/02; C07C 17/14; C07C 67/307
See application file for complete search history.

(56) References Cited

FOREIGN PATENT DOCUMENTS

| | | | |
|---|---|---|---|
| CN | 102295524 | * | 12/2011 |
| CN | 106831387 | | 6/2017 |
| WO | 0125191 | | 4/2001 |
| WO | 2013095699 | | 6/2013 |

OTHER PUBLICATIONS

CN 102295524 translated (Year: 2011).*
Huang et al. (Chemoselective Phototransformation of C—H Bonds on a Polymer Surface through a Photoinduced Cerium Recycling Redox Reaction, Chem. Eur. J., 20, p. 11421-11427, Published 2014) (Year: 2014).*
"International Search Report (Form PCT/ISA/210) of PCT/CN2017/107760," dated Dec. 27, 2017, with English translation thereof, pp. 1-4.

* cited by examiner

*Primary Examiner* — Yevgeny Valenrod
*Assistant Examiner* — Blaine G Doletski
(74) *Attorney, Agent, or Firm* — JCIP Global Inc.

(57) ABSTRACT

The present invention provides a direct oxidation method for saturated hydrocarbon bonds in an organic compound. The method allows an organic compound with a saturated hydrocarbon bond to react with an oxidizing reagent in the presence of cerium complex under visible light irradiation, thus oxidizing the saturated hydrocarbon bond to afford an oxidation product. The present reaction only needs to be carried out at room temperature, while the reaction efficiency remains high. In addition, only visible light is required to provide the energy for activation, rendering the present strategy is a milder and greener reaction method. The cerium catalyst used in the method is low in cost, simple and efficient, while the oxidizing reagent used is also stable in nature and low in industrial cost, rendering the catalytic system highly practical. Furthermore, environmental pollution caused by heavy transition metals and peroxides can be avoided in such strategy.

9 Claims, No Drawings

VISIBLE-LIGHT-INDUCED DIRECT OXIDATION METHOD FOR SATURATED HYDROCARBON BONDS

CROSS-REFERENCE TO RELATED APPLICATION

This application is a 371 application of International PCT application serial no. PCT/CN2017/107760, filed on Oct. 26, 2017, which claims the priority benefit of Chinese application no. 201710045228.6, filed on Jan. 19, 2017. The entirety of each of the above-mentioned patent applications is hereby incorporated by reference herein and made a part of this specification.

BACKGROUND

Technical Field

The present invention relates to the field of organic synthesis, and in particular, to a direct oxidation method for saturated hydrocarbon bonds in an organic compound, which is induced by visible light and efficiently catalyzed by a cerium complex.

Description of Related Art

Direct oxidation of hydrocarbon bonds in organic compounds has attracted increasing attention in the field of catalysis. The synthetic strategy is capable of directly converting widely existing hydrocarbon bonds into diverse functional groups (hydroxyl, carbonyl, amine, etc.). With inexpensive starting materials and significantly shortened synthetic routes, the synthetic strategy would be a promising choice for value-added drug molecules or intermediates thereof, and thus has broad application prospects in pharmaceutical industry. However, the high energy of such hydrocarbon bonds renders its activity relatively low. Existing processes typically require expensive transition metal catalysts, with the presence of less stable peroxides and frequently higher temperatures and pressures. Therefore, there has been a growing interest in designing efficient oxidation method for hydrocarbon bonds using only inexpensive catalysts and reagents under mild and green conditions. Visible-light-induced photoredox catalysis utilizes the energy of visible light to activate a photocatalyst, and thereby promotes organic reactions. Compared with the traditional catalysis, visible light catalysis requires only clean light energy, low catalyst dosage and mild reaction conditions, and it is expected to develop a more efficient and environmentally friendly synthesis method. Thus, it remains an imperative challenge to apply visible light catalysis to efficient oxidation reactions of saturated hydrocarbon bonds, aiming at developing a more economical and environmentally friendly photocatalytic strategy for industrial applications.

SUMMARY

An objective of the present invention is to provide a method for efficient oxidation of saturated hydrocarbon bonds in organic compounds, which utilizes inexpensive and readily available catalysts and reagents under mild conditions with visible light irradiation, the method produces the oxidation product with high yields and reduced waste emissions.

To accomplish the above objective, the present invention provides a visible-light-induced direct oxidation method for saturated hydrocarbon bonds. The method allows an organic compound with a saturated hydrocarbon bond to react with an oxidizing reagent in the presence of cerium complex and an additive under visible light irradiation, thus oxidizing the saturated hydrocarbon bond to afford an oxidation product.

Preferably, the organic compound is a paraffin hydrocarbon, a naphthenic hydrocarbon, an aromatic hydrocarbon, or other compounds containing a saturated hydrocarbon bond.

Preferably, the oxidizing reagent is oxygen, a halogenating reagent, or an azo reagent.

More preferably, the halogenating reagent is at least one of N-chlorosuccinimide, N-bromosuccinimide, p-toluenesulfonyl chloride, methanesulfonyl chloride, N-fluoropyridine, N-fluorodiphenylsulfonimide, 1-chloromethyl-4-fluoro-1,4-diazoniabicyclo[2.2.2]octane bis(tetrafluoroborate) salt, and elemental iodine.

More preferably, the azo reagent is at least one of azodicarbonate, azobenzene, azoformamide, and azodiisobutyronitrile.

Preferably, the metal cation of the cerium complex is any one of $Ce^{4+}$ and $Ce^{3+}$, preferably at least one of cerium tetrachloride hydrate, cerium tetrachloride, cerium trichloride hydrate, cerium trichloride, cerium nitrate hydrate, cerium trifluoromethanesulfonate, cerium tetrafluoromethanesulfonate, cerium sulfate, cerium acetate, cerium oxalate, and cerium tetraisopropoxide.

Preferably, the anion of the additive is any one of $Cl^-$ and $Br^-$, preferably at least one of tetrabutylammonium chloride, tetraethylammonium chloride, tetrabutylammonium bromide, tetraethylammonium bromide, tetrabutylphosphonium chloride, tetrabutylphosphonium bromide, sodium chloride, potassium chloride, cesium chloride, sodium bromide, potassium bromide, and cesium bromide.

Preferably, the molar ratio of the organic compound to the cerium complex is 1:0.0000001-0.2.

Preferably, the molar ratio of the cerium complex to the additive is 1:0.2-1:10.

Preferably, the reaction condition is from room temperature to 80° C.

Preferably, the visible light is light with a wavelength of 300-800 nm.

The cerium complex activates a hydrocarbon bond of an alkane under visible light irradiation to produce a highly reactive alkyl radical, and further reacts with an oxidizing reagent to obtain an oxidation product. The effect of the additive is to increase the catalytic efficiency of the cerium complex.

Compared with the prior art, the present invention has the following beneficial effects:

The present reaction only needs to be carried out at a relatively low temperature for short time, while the reaction efficiency remains high. In addition, only visible light is required to provide the energy for activation, rendering the present strategy a milder and greener reaction method. The cerium catalyst used in the method is low in cost, simple and efficient, while the oxidizing reagent used is also stable in nature and low in industrial cost. Furthermore, environmental pollution caused by heavy transition metals and peroxides can be avoided in such strategy.

DESCRIPTION OF THE EMBODIMENTS

The present invention is further illustrated below in conjunction with specific embodiments. It should be understood that these embodiments are merely illustrative of the present invention and are not intended to limit the scope of the present invention. In addition, it should be understood that after reading the instructions in the present invention, those skilled in the art may make various alterations and modifications to the present invention. These equivalent forms also fall within the scope defined by the claims appended hereto.

The respective raw materials, cerium complexes, and additives in the following embodiments are all commercially available products.

Embodiment 1

A visible-light-induced direct oxidation method for saturated hydrocarbon bonds, including the following specific steps:

Oxygen was introduced into 2 mL of a solution of ethylbenzene (106 mg, 1 mmol) in acetonitrile for 20 min, until the solution was saturated with the oxygen. Then 1 mol % cerium complex cerium trichloride (2.4 mg, 0.01 mmol) and 2 mol % additive tetrabutylammonium chloride (5.5 mg, 0.02 mmol) were added. After the addition, the ethylbenzene and the oxygen were allowed to react for 2 hrs in the presence of the cerium complex and the additive at room temperature (25° C.) under the irradiation of a blue LED lamp (wavelength of 380 nm-550 nm). With the hydrocarbon bond in the ethylbenzene oxidized, the oxidation product acetophenone was thus acquired. The reaction was as follows:

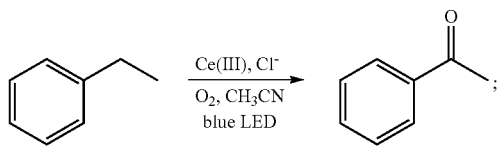

After the reaction had stopped, the mixture was diluted with dichloromethane, washed sequentially with water and saturated brine, and dried. After separation by column chromatography, the product acetophenone was obtained (108 mg, 90% yield). $^1$H NMR characterization data (500 MHz, with deuterated chloroform as a solvent) was: 7.96 (d, 2H), 7.68 (t, 1H), 7.46 (d, 2H), and 2.50 (s, 3H).

Embodiment 2

A visible-light-induced direct oxidation method for saturated hydrocarbon bonds, including the following specific steps:

Oxygen was introduced into 2 mL of a solution of cyclohexane (85 mg, 1 mmol) in acetonitrile for 20 min, until the solution was saturated with the oxygen. Then 1 mol % cerium complex cerium trichloride (2.4 mg, 0.01 mmol) and 2 mol % additive tetrabutylammonium chloride (5.5 mg, 0.02 mmol) were added. After the addition, the cyclohexane and the oxygen were allowed to react for 5 hrs in the presence of the cerium complex and the additive at room temperature (25° C.) under the irradiation of a blue LED lamp (wavelength of 380 nm-550 nm). With the hydrocarbon bond in the cyclohexane oxidized, the oxidation product cyclohexanol was thus acquired. The reaction was as follows:

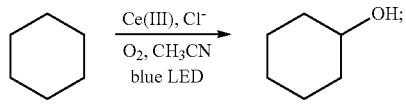

After the reaction had stopped, the mixture was diluted with dichloromethane, washed sequentially with water and saturated brine, and dried. After separation by column chromatography, the product cyclohexanol was obtained (88 mg, 88% yield). $^1$H NMR characterization data (500 MHz, with deuterated chloroform as a solvent) was: 4.80 (brs, 1H), 3.54 (m, 1H), 1.59 (m, 4H), and 1.45-1.5 (m, 6H).

Embodiment 3

A visible-light-induced direct oxidation method for saturated hydrocarbon bonds, including the following specific steps:

Oxygen was introduced into 2 mL of a solution of cyclohexane (85 mg, 1 mmol) in acetonitrile for 20 min, until the solution was saturated with the oxygen. Then 2 mol % cerium complex cerium nitrate (8.7 mg, 0.02 mmol) and 4 mol % additive tetrabutylammonium bromide (12.9 mg, 0.04 mmol) were added. After the addition, the cyclohexane and the oxygen were allowed to react for 48 hrs in the presence of the cerium complex and the additive at room temperature (25° C.) under the irradiation of a blue LED lamp (wavelength of 380 nm-550 nm). With the hydrocarbon bond in the cyclohexane oxidized, the oxidation product cyclohexanone was thus acquired. The reaction was as follows:

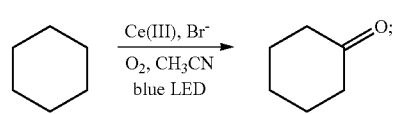

After the reaction had stopped, the mixture was diluted with dichloromethane, washed sequentially with water and saturated brine, and dried. After separation by column chromatography, the product cyclohexanone was obtained (80 mg, 82% yield). $^1$H NMR characterization data (500 MHz, with deuterated chloroform as a solvent) was: 2.33 (t, 4H), 1.86 (m, 4H), and 1.73 (m, 2H).

Embodiment 4

A visible-light-induced direct oxidation method for saturated hydrocarbon bonds, including the following specific steps:

P-toluenesulfonyl chloride (286 mg, 1.5 mmol), 1 mol % cerium complex cerium trichloride (2.4 mg, 0.01 mmol), and 2 mol % additive tetrabutylammonium chloride (5.5 mg, 0.02 mmol) were added to 2 mL of a solution of ethylbenzene (106 mg, 1 mmol) in acetonitrile, and then argon was bubbled for 20 min. Afterward, the ethylbenzene and the p-toluenesulfonyl chloride were allowed to react for 12 hrs in the presence of the cerium complex and the additive at room temperature (25° C.) under the irradiation of a blue LED lamp (wavelength of 380 nm-550 nm). With the saturated hydrocarbon bond in the ethylbenzene oxidized, an oxidation product was thus acquired. The reaction was as follows:

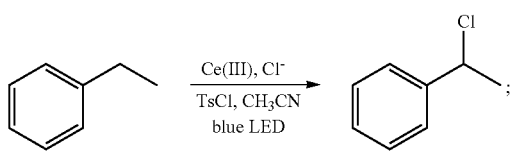

After the reaction had stopped, the mixture was diluted with dichloromethane, washed sequentially with water and saturated brine, and dried. After separation by column chromatography, the product 1-chloroethylbenzene was obtained (122 mg, 87% yield). $^1$H NMR characterization data (500 MHz, with deuterated chloroform as a solvent) was: 7.45-7.22 (m, 5H), 5.07 (q, 1H), and 1.82 (d, 3H).

Embodiment 5

A visible-light-induced direct oxidation method for saturated hydrocarbon bonds, including the following specific steps:

Diisopropyl azodicarboxylate (0.3 ml, 1.5 mmol), 1 mol % cerium complex cerium trichloride (2.4 mg, 0.01 mmol), and 5 mol % additive tetrabutylammonium chloride (14 mg, 0.05 mmol) were added to 10 mL of a solution of ethylbenzene (106 mg, 1 mmol) in acetonitrile, and then argon was bubbled for 20 min. Afterward, the ethylbenzene and the Diisopropyl azodicarboxylate were allowed to react for 10 hrs in the presence of the cerium complex and the additive at room temperature (25° C.) under the irradiation of a blue LED lamp (wavelength of 380 nm-550 nm). With the saturated hydrocarbon bond in the ethylbenzene oxidized, an oxidation product was thus acquired. The reaction was as follows:

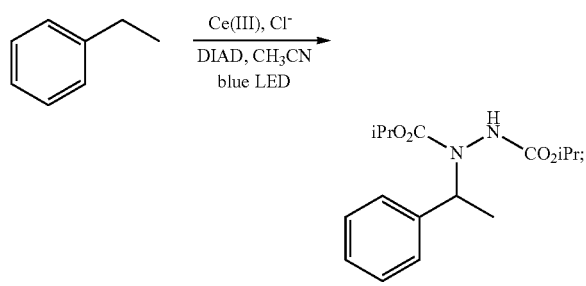

After the reaction had stopped, the mixture was diluted with dichloromethane, washed sequentially with water and saturated brine, and dried. After separation by column chromatography, the product was obtained (283 mg, 92% yield). $^1$H NMR characterization data (500 MHz, with deuterated chloroform as a solvent) was: 7.36 (m, 5H), 6.16 (brs, 1H), 5.5 (q, 1H), 5.0 (m, 2H), 1.55 (d, 3H), and 1.23 (d, 12H).

Embodiment 6

A visible-light-induced direct oxidation method for saturated hydrocarbon bonds, including the following specific steps:

N-fluorodiphenylsulfonimide (473 mg, 1.5 mmol), 2 mol % cerium complex cerium trichloride (4.8 mg, 0.02 mmol), and 4 mol % additive tetrabutylammonium chloride (11 mg, 0.04 mmol) were added to 5 mL of a solution of methyl valerate (116 mg, 1 mmol) in acetonitrile, and argon was bubbled for 20 min. Afterward, the methyl valerate and the N-fluorodibenzenesulfonimide were allowed to react for 20 hrs in the presence of the cerium complex and the additive at room temperature (25° C.) under the irradiation of a blue LED lamp (wavelength of 380 nm-550 nm). With the saturated hydrocarbon bond in the methyl valerate oxidized, an oxidation product was thus acquired. The reaction was as follows:

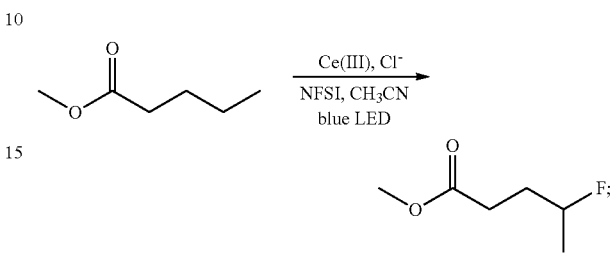

After the reaction had stopped, the mixture was diluted with dichloromethane, washed sequentially with water and saturated brine, and dried. After separation by column chromatography, the product was obtained (110 mg, 82% yield). $^1$H NMR characterization data (500 MHz, with deuterated acetonitrile as a solvent) was: 4.72 (dm, 1H), 3.66 (s, 3H), 2.47-2.42 (m, 2H), 1.95-1.84 (m, 2H), and 1.32 (dd, 3H).

Embodiment 7

A visible-light-induced direct oxidation method for saturated hydrocarbon bonds, including the following specific steps:

Oxygen was introduced into 10 mL of a solution of methyl valerate (116 mg, 1 mmol) in acetonitrile for 20 min, until the solution was saturated with the oxygen. Then 2 mol % cerium complex cerium trichloride (4.8 mg, 0.02 mmol) and 5 mol % additive tetrabutylammonium chloride (14 mg, 0.05 mmol) were added. After the addition, the methyl valerate and the oxygen were allowed to react for 12 hrs in the presence of the cerium complex and the additive at room temperature (25° C.) under the irradiation of a blue LED lamp (wavelength of 380 nm-550 nm). With the saturated hydrocarbon bond in the methyl valerate oxidized, an oxidation product was thus acquired. The reaction was as follows:

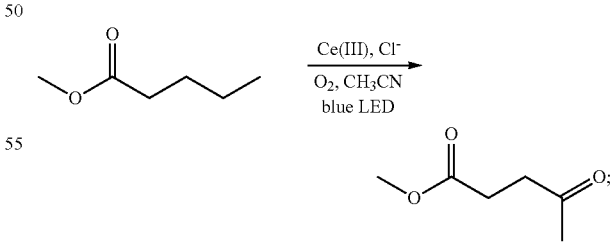

After the reaction had stopped, the mixture was diluted with dichloromethane, washed sequentially with water and saturated brine, and dried. After separation by column chromatography, the product was obtained (100 mg, 77% yield). $^1$H NMR characterization data (500 MHz, with deuterated chloroform as a solvent) was: 3.64 (s, 3H), 2.73 (t, 2H), 2.54 (t, 2H), and 2.16 (s, 3H).

Embodiment 8

A visible-light-induced direct oxidation method for saturated hydrocarbon bonds, including the following specific steps:

Oxygen was introduced into 20 mL of a solution of indane (119 mg, 1 mmol) in acetonitrile for 20 min, until the solution was saturated with the oxygen. Then 2 mol % cerium complex cerium nitrate (8.7 mg, 0.02 mmol) and 4 mol % of additive tetrabutylammonium bromide (13 mg, 0.04 mmol) were added. After the addition, the indane and the oxygen were allowed to react for 2 hrs in the presence of the cerium complex and the additive at room temperature (25° C.) under the irradiation of a blue LED lamp (wavelength of 380 nm-550 nm). With the saturated hydrocarbon bond in the indane oxidized, an oxidation product was thus acquired. The reaction was as follows:

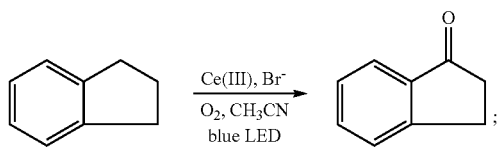 [SMILES: c1ccc2c(c1)CCC2 ; O=C1CCc2ccccc21]

After the reaction had stopped, the mixture was diluted with dichloromethane, washed sequentially with water and saturated brine, and dried. After separation by column chromatography, the product was obtained (106 mg, 80% yield). $^1$H NMR characterization data (500 MHz, with deuterated chloroform as a solvent) was: 7.41-7.0 (m, 4H), 2.94 (t, 2H), and 2.61 (t, 2H).

Embodiment 9

A visible-light-induced direct oxidation method for saturated hydrocarbon bonds, including the following specific steps:

N-bromosuccinimide (356 mg, 2 mmol), 2 mol % cerium complex cerium nitrate (8.7 mg, 0.02 mmol), and 4 mol % additive tetrabutylammonium bromide (13 mg, 0.04 mmol) were added to 10 mL of a solution of indane (119 mg, 1 mmol) in acetonitrile. Afterward, the indane and the N-bromosuccinimide were allowed to react for 12 hrs in the presence of the cerium complex and the additive at room temperature (25° C.) under the irradiation of a blue LED lamp (wavelength of 380 nm-550 nm). With the saturated hydrocarbon bond in the indane oxidized, an oxidation product was thus acquired. The reaction was as follows:

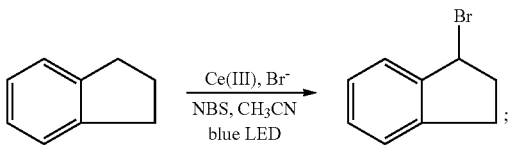 [SMILES: c1ccc2c(c1)CCC2 ; BrC1CCc2ccccc21]

After the reaction had stopped, the mixture was diluted with dichloromethane, washed sequentially with water and saturated brine, and dried. After separation by column chromatography, the product was obtained (165 mg, 84% yield). $^1$H NMR characterization data (500 MHz, with deuterated chloroform as a solvent) was: 7.18-7.16 (m, 1H), 7.01-6.98 (m, 3H), 5.33 (dd, 1H), 2.99 (m, 1H), 2.67 (m, 1H), and 2.39 (m, 2H).

What is claimed is:

1. A visible-light-induced direct oxidation method for saturated hydrocarbon bonds, comprising: allowing an organic compound with a saturated hydrocarbon bond to react with an oxidizing reagent in the presence of cerium complex and an additive under visible light irradiation, thus oxidizing the saturated hydrocarbon bond to afford an oxidation product, and wherein an anion of the additive is any one of Cl$^-$ and Br$^-$.

2. The visible-light-induced direct oxidation method for saturated hydrocarbon bonds according to claim 1, wherein the organic compound is paraffin hydrocarbon, naphthenic hydrocarbon, aromatic hydrocarbon, or other compounds containing a saturated hydrocarbon bond.

3. The visible-light-induced direct oxidation method for saturated hydrocarbon bonds according to claim 1, wherein the oxidizing reagent is oxygen, a halogenating reagent, or an azo reagent.

4. The visible-light-induced direct oxidation method for saturated hydrocarbon bonds according to claim 3, wherein the halogenating reagent is at least one of N-chlorosuccinimide, N-bromosuccinimide, p-toluenesulfonyl chloride, methanesulfonyl chloride, N-fluoropyridine, N-fluorodiphenylsulfonimide, 1-chloromethyl-4-fluoro-1,4-diazoniabicyclo[2.2.2]octane bis(tetrafluoroborate) salt, and elemental iodine.

5. The visible-light-induced direct oxidation method for saturated hydrocarbon bonds according to claim 3, wherein the azo reagent is at least one of azodicarbonate, azobenzene, azoformamide, and azodiisobutyronitrile.

6. The visible-light-induced direct oxidation method for saturated hydrocarbon bonds according to claim 1, wherein a metal cation of the cerium complex is any one of Ce$^{4+}$ and Ce$^{3+}$.

7. The visible-light-induced direct oxidation method for saturated hydrocarbon bonds according to claim 1, wherein a molar ratio of the organic compound to the cerium complex is 1:0.0000001-0.2.

8. The visible-light-induced direct oxidation method for saturated hydrocarbon bonds according to claim 1, wherein a reaction condition is from room temperature to 80° C.

9. The visible-light-induced direct oxidation method for saturated hydrocarbon bonds according to claim 1, wherein the visible light is light with a wavelength of 300-800 nm.

* * * * *